United States Patent
Meert et al.

(10) Patent No.: US 6,403,589 B1
(45) Date of Patent: Jun. 11, 2002

(54) METHOD OF TREATING PAIN WITH DRAFLAZINE-ANALOGUES

(75) Inventors: Theo Frans Meert, Boom; Herman Van Belle, Vosselaar, both of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/446,140

(22) PCT Filed: Jun. 9, 1998

(86) PCT No.: PCT/EP98/03664
§ 371 (c)(1),
(2), (4) Date: Dec. 15, 1999

(87) PCT Pub. No.: WO98/57643
PCT Pub. Date: Dec. 23, 1998

(30) Foreign Application Priority Data

Jun. 19, 1997 (EP) .............................. 97201813

(51) Int. Cl.⁷ .................. A61K 31/50; A61K 31/495
(52) U.S. Cl. ............ 514/252.14; 514/252.12; 514/255.04
(58) Field of Search ................ 514/252.12, 252.14, 514/255.04

(56) References Cited

U.S. PATENT DOCUMENTS 5,236,908 A  8/1993  Gruber et al. .............. 514/46

FOREIGN PATENT DOCUMENTS

| EP | 0 068 544 | 1/1983 |
| EP | 0 285 219 | 10/1988 |
| FR | 2 368 280 | 5/1978 |
| GB | 2 105 988 | 4/1983 |
| WO | WO 94/18200 | 8/1994 |
| WO | WO 94/18200 A1 * | 8/1994 |

OTHER PUBLICATIONS

Turker et al., "Analgesic action of Lidoflazine (R 7904)", European Journal of Pharmacology 11 pp. 90–95, 1970.*
Abstract: Dialog IP Document; Aspirin and disyridamole salt compsn.—having blood platelet aggregate; Patent Assignee: THERAMEX SA, 1989.
IJzerman et al.; Inhibition of neculeoside transport by a new series of compounds related to lidoflazine and mioflazine; European Journal of Phrm–Molecular Pharma Section, 172 (1989) pp. 273–281.
Andersen et al.; Nucleoside transport inhibition by draflzaine in unstable coronary disease; Eur J. Clin Pharmacol (1996) 51: pp 7–13.
Turker et al.; Analgesic action of lidoflazine (R7904); Eur J of Pharmac 11 (1970) pp 90–95.

* cited by examiner

Primary Examiner—Dwayne C. Jones
(74) Attorney, Agent, or Firm—Ellen Ciambrone Coletti

(57) ABSTRACT

This invention concerns the use of nucleoside transport inhibitors, more particularly compounds of formula

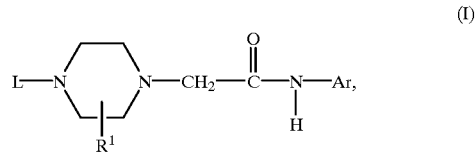
(I)

an N-oxide form, a pharmaceutically acceptable acid addition salt or a stereochemically isomeric form thereof, wherein $R^1$ is $C_{1-4}$alkyl, aminocarbonyl or mono- or di($C_{1-4}$alkyl)aminocarbonyl, Ar is a phenyl or pyridinyl derivative and L is a radical of formula

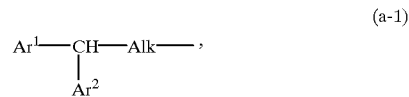
(a-1)

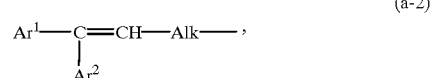

(a-2)

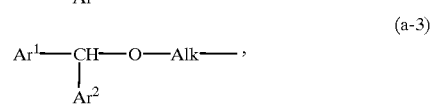

(a-3)

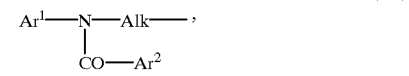

(a-4)

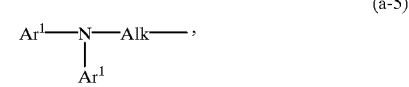

(a-5)

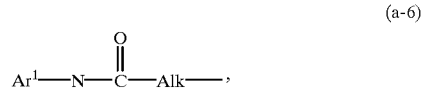

(a-6)

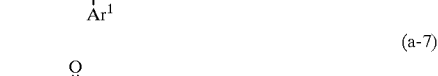

(a-7)

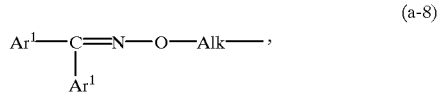

(a-8)

wherein $Ar^1$ is a phenyl derivative; $Ar^2$ is a phenyl or pyridinyl derivative; and Alk is $C_{1-4}$alkanediyl; for the manufacture of a medicine for the treatment of warm-blooded animals suffering from pain.

10 Claims, No Drawings

METHOD OF TREATING PAIN WITH DRAFLAZINE-ANALOGUES

CROSS REFERENCE TO RELATED APPLICATIONS

This application is the national stage of application Ser. No. PCT/EP98/03664, filed on Jun. 9, 1998 which application claims priority from EP No. 97201813.9, filed on Jun. 16, 1997.

The present invention is concerned with the use of nucleoside transport inhibitors, in particular compounds of formula (I) for the manufacture of a medicament for the treatment of warm-blooded animals, including humans, suffering from chronic pain conditions, such as neuropathic pain.

Nucleoside Transport Inhibition

Nucleoside transport inhibition is a pharmacological activity mainly associated with treatment of problems arising during myocardial ischemia and reperfusion. Indeed adenosine exhibits a multitude of pharmacological properties which makes it particularly suitable for tackling the above mentioned problems. The nucleoside transporter plays a key role in the catabolism and fate of endogenous adenosine, produced in the interstitial space during ischemia. Being located almost exclusively in endothelial cells lining the vasculature, this transporter facilitates diffusion according to the existing gradient. Hence, because of extensive catabolism within these cells, the transporter accelerates adenosine breakdown. In addition, if perfusion prevails or during reperfusion, when the vascular compartment constitutes a major sink, the transporter will carry the adenosine, surviving intra-endothelial metabolism, into the lumen and enhance the washout. Paracellular passage (via clefts in between the endothelial layer) seems to be a very slow process, so that the main escape of adenosine (and inosine) through the endothelial barrier depends on a functioning transporter. While not provoking adenosine formation, inhibition of the transporter will considerably prolong the presence of adenosine at its site of formation by preventing uptake and catabolism in the endothelial cells.

An overview of how nucleoside transport inhibition can be experimentally determined is given in "Comparative pharmacology of nucleoside transport inhibitors" in *Nucleosides and Nucleotides* 10:975–982, 1991 (Van Belle H, Janssen P A J).

Known potent nucleoside transport inhibitors are dipyridamole, dilazep, and members of lidoflazine family (e.g. lidoflazine, mioflazine, sofluflazine, R 75231 and draflazine, which is the (−)-enantiomer of R 75231).

The only nucleoside transport inhibitor thus far approved for human therapy is dipyridamole. The mean therapeutic uses for dipyridamole are the prophylaxis of angina pectoris and as an antithrombotic.

Other nucleoside transport inhibitors are the compounds of formula (I) as shown hereinafter.

Some compounds of formula (I) are disclosed in the prior art as inhibitors of nucleoside transport through membranes, in particular 3-(aminocarbonyl)-4-[4,4-bis(4-fluorophenyl)-butyl]-N-(2,6-dichlorophenyl)-1-piperazineacetamide dihydrochloride monohydrate, generically known as mioflazine, is described in *Molecular Physiology* 8:615–630 (1985). In EP-A-0,068,544, published on Jan. 5, 1983, and WO-91/07967, published on Jun. 13, 1991, N-arylpiperazinealkanamides, in particular S-(−)-2-(aminocarbonyl)-N-(4-amino-2,6-dichlorophenyl)-4-[5,5-bis(4-fluorophenyl)-pentyl]-1-piperazineacetamide, generically known as draflazine, are disclosed as agents useful for protecting the heart from myocardial injury caused by ischaemia or hypoxia. EP-A-0,285,219, published on Oct. 5, 1988, discloses N-aryl-piperazine-alkanamides for improving sleep or counteracting sleep disorders.

In the *European Journal of Pharmacology*, vol 11, no 1, Jul. 1, (1970) Türker et al. disclose lidoflazine significantly increased reaction time of mice to thermal stimulation and increased pain treshold to electrical stimulation of incisor teeth in rabbits, but not of canine teeth in dogs. The pain stimuli used in these models are typically acute pain stimuli. These types of pain are not related to chronic pain conditions, more particularly neuropatic pain.

In the *Eur. J. Pharmacol., Mol. Pharmacol. Sect.*,1989, 273–81, Ijzerman et al introduce a new series of compounds related to the nucleoside transport inhibitors, lidoflazine and mioflazine. The article does not mention any relationship between these compounds and pain, more specifically chronic pain conditions, more particularly neuropathic pain.

In the European Journal of Clinical Pharmacology, 51(1) (1996) 7–13 Andersen et al discuss a randomized, double-blind, placebo-controlled study, wherein the tolerability and safety of draflazine in the treatment of patients with unstable angina was evaluated. The article discloses that the mean duration of chest pain during the 24 hour observation period was 91.4 min in the placebo group (i.e. the group not treated with draflazine) compared to 75.5 min in draflazine treated patients. The chest pain experienced by these patients is not a chronic pain condition, more particularly neuropathic pain.

Surprisingly it has now been found that the compounds of formula (I) are useful for the treatment of warm-blooded animals suffering from chronic pain conditions such as neuropatic pain, inflammatory pain and cancer pain.

The present invention concerns the use of nucleoside transport inhibitors, and especially the compounds of formula

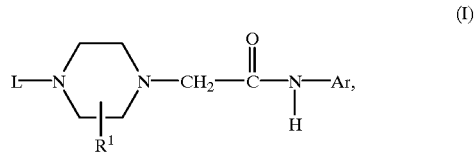

the N-oxide forms, the pharmaceutically acceptable acid addition salts and the stereochemically isomeric forms thereof, wherein $R^1$ is $C_{1-4}$alkyl, aminocarbonyl or mono- or di($C_{1-4}$alkyl)aminocarbonyl;

L is a radical of formula

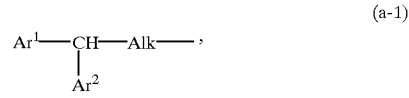

(a-1)

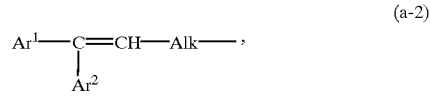

(a-2)

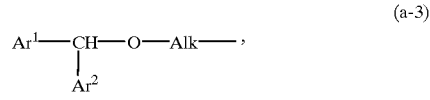

(a-3)

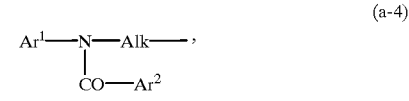

(a-4)

-continued (a-5)
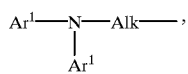

(a-6)
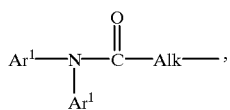

(a-7)
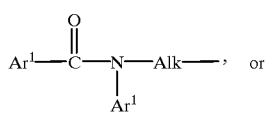 or (a-8)
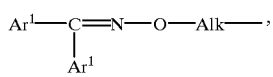

wherein
Ar$^1$ is phenyl, phenyl substituted with halo or C$_{1-4}$alkyloxy;
Ar$^2$ is phenyl; phenyl substituted with halo, C$_{1-4}$alkyloxy; or pyridinyl;
Alk is C$_{1-4}$alkanediyl;
Ar is a radical of formula (b-1)
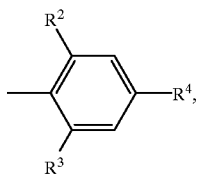

(b-2)
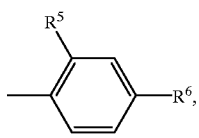

(b-3)
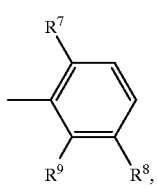

(b-4)
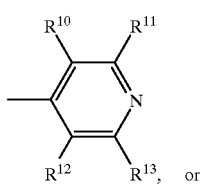 or

-continued (b-5)
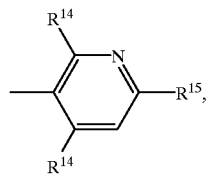

wherein
R$^2$ and R$^3$ each independently are halo or C$_{1-4}$alkyl;
R$^4$ is hydrogen, halo, nitro, amino, mono- or di(C$_{1-4}$alkyl)amino, C$_{1-4}$alkylcarbonylamino, aminocarbonylamino, C$_{1-4}$alkyl, C$_{1-4}$alkyloxy, C$_{1-4}$alkyloxycarbonyl, C$_{1-4}$alkylcarbonyl, aminocarbonyl, mono- or di(C$_{1-4}$alkyl)aminocarbonyl, cyano or aminomethyl;
R$^5$ is C$_{1-4}$alkylcarbonyl;
R$^6$ is hydrogen, amino, mono- or di(C$_{1-4}$alkyl)amino, C$_{1-4}$alkylcarbonylamino, aminocarbonylamino, aminocarbonyl or cyano;
R$^7$ is C$_{1-4}$alkyl;
R$^8$ is halo or C$_{1-4}$alkylcarbonyl;
R$^9$ is hydrogen or C$_{1-4}$alkyl;
R$^{10}$ is halo or C$_{1-4}$alkyl;
R$^{11}$ is hydrogen, hydroxy or C$_{1-4}$alkyl;
R$^{12}$ is halo or C$_{1-4}$alkyl;
R$^{13}$ is hydrogen or;
R$^{12}$ and R$^{13}$ taken together may also form a C$_{3-5}$alkanediyl radical;
each R$^{14}$ is C$_{1-4}$alkyl; and
R$^{15}$ is C$_{1-4}$alkyl or amino;
for the manufacture of a medicine for the treatment of warm-blooded animals suffering from pain.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; C$_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; C$_{3-5}$alkanediyl defines bivalent straight and branched chain saturated hydrocarbon radicals having from 3 to 5 carbon atoms such as, for example, 1,3-propanediyl, 1,4-butanediyl, 1,5-pentanediyl and the like.

The pharmaceutically acceptable acid addition salts as mentioned hereinabove are meant to comprise the therapeutically active non-toxic acid addition salt forms which the compounds of formula (I) are able to form. The compounds of formula (I) which appear in their free form as a base can be converted in their acid addition salt by treating said free base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

Some compounds of the present invention may exist in different tautomeric forms and all such tautomeric forms are intended to be included within the scope of the present invention. For instance, compounds of formula (I) wherein Ar is a radical of formula (b-4), i.e. a pyridinyl, substituted with hydroxy, may exist in their corresponding tautomeric form.

The term stereochemically isomeric forms as used hereinbefore defines the possible different isomeric as well as conformational forms which the compounds of formula (I) may possess. Unless otherwise mentioned or indicated, the chemical designation of compounds denotes the mixture, in particular the racemic mixture, of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein the piperazine-nitrogen is N-oxidized.

A particular group of compounds of formula (I) are those wherein
$R^1$ is aminocarbonyl or ($C_{1-4}$alkyl)aminocarbonyl;
L is a radical of formula (a-1) or (a-2) wherein
$Ar^1$ is phenyl or phenyl substituted with halo;
$Ar^2$ is phenyl, phenyl substituted with halo, or pyridinyl;
Alk is $C_{1-4}$alkanediyl;
Ar is a radical of formula b-1) or (b-3) wherein
$R^2$ and $R^3$ each independently are halo or $C_{1-4}$alkyl;
$R^4$ is hydrogen, $C_{1-4}$alkyl, halo, nitro, amino, cyano or aminocarbonyl;
$R^7$ is $C_{1-4}$alkyl;
$R^8$ is halo or $C_{1-4}$alkylcarbonyl; and
$R^9$ is hydrogen or $C_{1-4}$alkyl.

A more particular group of compounds are those particular compounds wherein
$R^1$ is aminocarbonyl or methylaminocarbonyl;
L is a radical of formula (a-1) or (a-2) wherein
$Ar^1$ is phenyl or phenyl substituted with fluoro, in particular 4-fluoro;
$Ar^2$ is phenyl, phenyl substituted with fluoro, in particular 4-fluoro, or pyridinyl;
Alk is $C_{3-4}$alkanediyl;
Ar is a radical of formula (b-1) or (b-3) wherein
$R^2$ and $R^3$ each independently are chloro or methyl;
$R^4$ is hydrogen, methyl, chloro, amino, cyano or aminocarbonyl;
$R^7$ is methyl;
$R^8$ is chloro or methylcarbonyl; and
$R^9$ is hydrogen.

Most preferred compounds of formula (I) are
2-(aminocarbonyl)-N-(4-amino-2,6-dichlorophenyl)-4-[5,5-bis(4-fluorophenyl)-pentyl]-1-piperazineacetamide; and S-(−)-2-(aminocarbonyl)-N-(4-amino-2,6-dichlorophenyl)-4-[5,5-bis(4-fluorophenyl)-pentyl]-1-piperazineacetamide; the stereoisomeric forms, the pharmaceutically acceptable acid addition salts and the N-oxide forms thereof.

Novel compounds of formula (I) are 3-(aminocarbonyl)-N-(2,6-dichloro-phenyl)-4-[4-(4-fluorophenyl)-4-(3-pyridinyl)-butyl]-1-piperazineacetamide, and N-(2-acetyl-6-chlorophenyl)-4-[5,5-bis(4-fluorophenyl)-4-pentenyl]-3-[(methyl-amino)carbonyl]-1-piperazineacetamide.

The compounds of formula (I) can be prepared as described in EP-0,068,544, EP-A-0,285,219, U.S. Pat. Nos. 4,968,684, 5,026,853 and EP-A-0,455,789. In general, they can be prepared by N-alkylating an intermediate of formula (II) with an intermediate of formula (III), or by N-alkylating an intermediate of formula (IV) with an intermediate of formula (V).

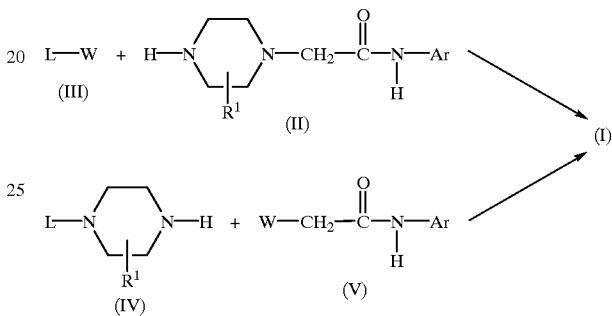

In the above reaction scheme, W is an appropriate leaving group such as, for example, chloro, bromo, methanesulfonyloxy or benzenesulfonyloxy. The reaction can be performed in a reaction-inert solvent such as, for example, toluene, dichloromethane, methyl isobutylketone, N,N-dimethylacetamide or N,N-dimethylformamide, in the presence of a suitable base such as, for example, sodium carbonate, sodium hydrogen carbonate or triethylamine, and optionally in the presence of potassium iodide. Stirring may enhance the rate of the reaction. The reaction may conveniently be carried out at a temperature ranging between room temperature and reflux temperature of the reaction mixture.

The compounds of formula (I) can also be converted into each other following art-known procedures of functional group transformations.

The preparation of intermediates of formula (II), (III), (IV) and (V) is described in EP-0,068,544, EP-A-0,285,219, U.S. Pat. Nos. 4,968,684 and 5,026,853.

Compounds of formula (I) and some of the intermediates in the present invention contain at least one asymmetric carbon atom in their structure, namely the piperazine carbon atom bearing the $R^1$-radical which may be present in a R- or S-configuration. Consequently, the compounds of formula (I) may be present in two different enantiomeric forms, which may be separated from each other. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. An alternative manner of separating the enantiomeric forms of the compounds of formula (I) and intermediates involves liquid chromatography, in particular liquid chromatography using a chiral stationary phase.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed, in particular racemic, stereochemically isomeric forms of the compounds of formula (I) are intended to be embraced within the scope of the present invention.

The pain-relieving properties of the compounds of formula (I) are illustrated by the "Formalin test on guinea pigs", described in Example B.1, which demonstrates the acute and chronic pain-relieving effect of the subject compounds.

In view of their favourable pain-relieving properties, the compounds of formula (I), the pharmaceutically acceptable addition salts, stereochemically isomeric forms and N-oxide forms thereof, are useful to treat or relieve warm-blooded animals suffering from chronic pain conditions, such as neuropathic pain, inflammatory pain, cancer pain. These conditions are related to hyperalgesia and allodynia. These conditions might include acute pain, skeletal muscle pain, low back pain, upper extremity pain, fibromyalgia and myofascial pain syndromes, orofacial pain, abdominal pain, phantom pain, tic douloureux and atypical face pain, nerve root damage and arachnoiditis, geriatric pain, central pain, inflammatory pain.

In particular, the subject compounds are useful to treat chronic non-cancer pain such as, neuropathic pain. Neuropathic pain results from lesions in the peripheral or central nervous system. It is often associated with somatosensory deficits and the distribution of pain is mostly related to the area of somatosensory dysfunction. The onset of the pain can be delayed after the causative event, even up to months or years. There are several causes of neuropathic pain with a considerable variability in symptoms and neurological deficits. Examples are peripheral nerve damage due to traumatic injury compression, ischemia, toxins, nutritional deficiencies, infections and complications of liver and kidney.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount of a compound of formula (I) would be from 0.001 mg/kg to 100 mg/kg body weight, and in particular from 0.01 mg/kg to 10 mg/kg body weight. It may be appropriate to administer the required dose as two, three, four or more sub-doses at appropriate intervals throughout the day. Said sub-doses may be formulated as unit dosage forms, for example, containing 0.1 to 500 mg, and in particular 1 mg to 200 mg of compound of formula (I) per unit dosage form. In particular, said sub-doses are formulated as an oral dosage form being either a solid such as, e.g. tablets (both swallowable-only and chewable forms), capsules, gelcabs and the like, or a liquid.

The compounds of formula (I), the pharmaceutically acceptable addition salts, stereochemically isomeric forms and N-oxide forms thereof, may conveniently be used in combination with an analgesic such as, for example, non-narcotic analgesics, e.g. aspirin or acetaminophen; NSAIDS (nonsteroidal antiinflammatory drugs), e.g. ibuprofen, naproxen, fenoprofen, ketoprofen, flurbiprofen, fenbufen, indomethacin and the like; opioids, e.g. codeine, morphine, naloxone, buprenorphine, pentazocine, fentanyl and the like; antidepressants, e.g. doxepin, fluoxetine, paroxetine and the like; ion channel modulators and/or membrane stabilising agents, e.g. lidocaine or mexiletine; α2-adrenergic agonists, e.g. clonidine; capsaicin analogues; or NMDA (N-methyl-D-aspartate) receptor antagonists, e.g. ketamine. The invention thus provides a combination comprising a composition as defined herein, together with an analgesic. The combination may be administered separately, simultaneously, concurrently or consecutively by any of the routes described above, or the combination may also be presented in the form of one pharmaceutical formulation. Thus, a pharmaceutical product comprising (a) a compound of formula (I) and (b) an analgesic as defined hereinbefore, as a combined preparation for simultaneous, separate or sequential use in the treatment of warm-blooded animals suffering from pain. Such a product may comprise a kit comprising a container containing a pharmaceutical composition of a compound of formula (I), and another container comprising a pharmaceutical composition of the analgesic. The product with separate compositions of the two active ingredients has the advantage that appropriate amounts of each component, and timing and sequence of administration can be selected in function of the patient.

When compounds of formula (I) are used in combination with an analgesic, the dose of the analgesic may vary from the dose when used alone. Thus when compounds of formula (I) are used together with an analgesic the dose of the latter may be the same or more commonly, lower, than the dose employed when the analgesic is used alone. Appropriate doses will be readily appreciated by those skilled in the art.

In view of the above uses of the compounds of formula (I), it follows that the present invention also provides a method of treating warm-blooded animals suffering from pain, said method comprising the oral or systemic administration of a therapeutic amount of a compound of formula (I) effective in relieving pain.

The following examples are intended to illustrate and not to limit the scope of the present invention.

EXPERIMENTAL PART

Hereinafter "THF" means tetrahydrofuran, "DCM" means dichloromethane, "DIPE" means diisopropylether, "DMF" means N,N-dimethylformamide and "MIK" means methyl isobutyl ketone.

A. Preparation of the Final Compounds

Example A.1

A mixture of 6.7 g of 1,1'-(4-iodobutylidene)bis[4-fluorobenzene], 5.2 g of 3-[(methylamino)carbonyl]-N-(2,4,6-trimethylphenyl)-1-piperazineacetamide, 2.3 g sodium carbonate and 38 ml DMF is stirred for 18 hours at 70° C. The reaction mixture is cooled and poured onto ice-water. The product is extracted with DCM. The extract is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is dried, yielding 4.23 g of 4-[4,4-bis(4-fluorophenyl)butyl]-3-[(methylamino)-carbonyl]-N-(2,4,6-trimethylphenyl)-1-piperazineacetamide (compound 1, mp. 82.3° C.).

Example A.2

A mixture of 5.8 g of 4-[4,4-bis(4-fluorophenyl)butyl]-N-methyl-2-piperazine-carboxamide, 3.6 g of 2-chloro-N-(2,4,6-trimethylphenyl)acetamide, 2.12 g of sodium carbonate and 150 ml of MIK is stirred and refluxed for 18 hours. The reaction mixture is cooled and washed with water. The organic phase is dried, filtered and evaporated. The residue is purified by column-chromatography over silica gel using a mixture of trichloromethane and methanol (95:5 by volume) as eluent. The pure fractions are collected and the eluent is evaporated. The residue is dried, yielding 4.34 g of 4-[4,4-bis(4-fluorophenyl)butyl]-2-[(methylamino)carbonyl]-N-(2,4,6-trimethylphenyl)-1-piperazineacetamide (compound 2, mp. 90.2° C.).

Example A.3

A mixture of 1-[4-(4-fluorophenyl)-4-(3-pyridinyl)butyl]-2-piperazinecarboxamide (6.75 g), 2-chloro-N-(2,6-dichlorophenyl)acetamide (5.24 g), sodium carbonate (3.16 g) and DMF (143 ml) was stirred for 4 hours at 70° C. The reaction mixture was evaporated and water was added to the residue. After extraction with DCM, the combined organic layers were washed with water, dried, filtered and evaporated. The residue was purified by column chromatography over silica gel (eluent:CHCl$_3$/CH$_3$OH 95/5). The desired fractions were collected and the solvent was evaporated. The residue was dissolved in 2-propanol and DIPE and converted into the hydrochloride salt. The salt was filtered off and dried, yielding 2.23 g of 3-(amino-carbonyl)-N-(2,6-dichloro-phenyl)-4-[4-(4-fluorophenyl)-4-(3-pyridinyl)-butyl]-1-piperazineacetamide dihydrochloride.monohydrate (compound 14, mp. 226.3° C.).

Example A.4

A mixture of (±)-1-[5,5-bis(4-fluorophenyl)-4-pentenyl]-N-methyl-2-piperazine-carboxamide (4 g), N-(2-acetyl-6-chlorophenyl)-2-chloroacetamide (3.2 g) and triethyl amine (75 ml) in DMF (75 ml) was stirred for 3 hours at 70° C. The solvent was evaporated. The residue was purified by column chromatography over silica gel (eluent:CH$_2$Cl$_2$/CH$_3$OH 97/3). The desired fractions were collected and the solvent was evaporated. The residue was dissolved in 2-propanol and converted into the ethanedioic acid salt (1:2). The salt was filtered off and dried (vacuum; 70° C.), yielding 3.72 g of (±)-N-(2-acetyl-6-chlorophenyl)-4-[5,5-bis(4-fluorophenyl)-4-pentenyl]-3-[(methylamino)carbonyl]-1-piperazineacetamide ethanedioate (1:2) (compound 18, mp. 140° C.).

Tables 1 to 3 list the compounds that were prepared according to one of the above Examples.

TABLE 1

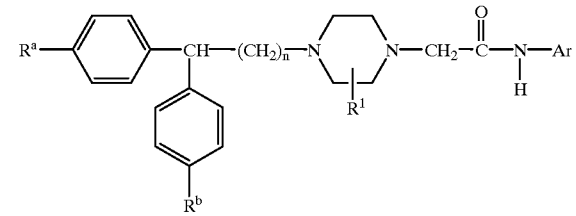

| Co. No | Ex. No. | R$^a$ | R$^b$ | n | R$^1$ | Ar | Physical data |
|---|---|---|---|---|---|---|---|
| 1 | 1 | F | F | 3 | 3-CONHCH$_3$ | 2,4,6-tri-methyl-phenyl | mp. 82.3° C. |
| 2 | 2 | F | F | 3 | 2-CONHCH$_3$ | 2,4,6-tri-methyl-phenyl | mp. 90.2° C. |
| 3 | 2 | F | F | 3 | 3-CONHCH$_3$ | 5-chloro-2-methyl-phenyl | .2HCl; mp. 190–225° C. |
| 4 | 2 | F | F | 3 | 2-CONHCH$_3$ | 5-chloro-2-methyl-phenyl | mp. 146.3° C. |
| 5 | 2 | F | F | 4 | 2-CONH$_2$ | 2,6-dichloro-phenyl | .2HCl; mp. 178.1° C. |
| 6 | 2 | H | H | 4 | 2-CONH$_2$ | 2,6-dichloro-phenyl | mp. 149.6° C. |
| 7 | 1 | F | F | 4 | 3-CONH$_2$ | 2,6-dichloro-phenyl | .2HCl.H$_2$O; mp. 206.2° C. |
| 8 | 2 | F | F | 4 | 2-CONH$_2$ | 2,6-trichloro-phenyl | mp. 117.2° C. |
| 9 | 1 | F | F | 4 | 3-CONH$_2$ | 2,6-dichloro-4-cyano-phenyl | .2HCl.H$_2$O; mp. 192.7° C. |

TABLE 1-continued

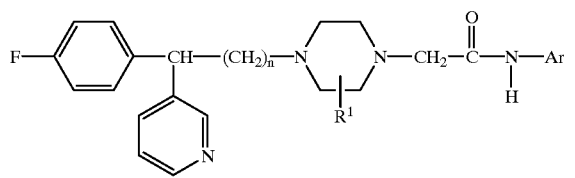

| Co. No | Ex. No | R^a | R^b | n | R^1 | Ar | Physical data |
|---|---|---|---|---|---|---|---|
| 10 | 1 | F | F | 4 | 3-CONH$_2$ | 4-aminocarbonyl-2,6-dichlorophenyl | mp. 123.7° C. |
| 11 | 1 | F | F | 4 | 2-CONH$_2$ | 4-amino-2,6-dichlorophenyl | — |
| 12 | 1 | F | F | 4 | 2-CONH$_2$ | 4-amino-2,6-dichlorophenyl | R-(+)-; mp. 119.1° C. |
| 13 | 1 | F | F | 4 | 2-CONH$_2$ | 4-amino-2,6-dichlorophenyl | S-(−)-; mp. 124.1° C. |

TABLE 2

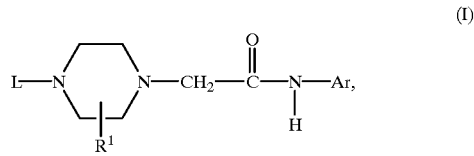

| Co. No | Ex. No | n | R^1 | Ar | Physical data (mp. in ° C.) |
|---|---|---|---|---|---|
| 14 | 3 | 3 | 3-CONH$_2$ | 2,6-dichlorophenyl | .2HCl.H$_2$O; mp. 226.3° C. |
| 15 | 1 | 4 | 3-CONH$_2$ | 4-aminocarbonyl-2,6-dichlorophenyl | .3HCl.2H$_2$O; mp. 173.0° C. |

TABLE 3

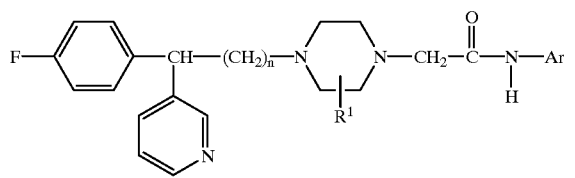

| Co. No | Ex. No | R^a | R^b | n | R^1 | Ar | Physical data (mp. in ° C.) |
|---|---|---|---|---|---|---|---|
| 16 | 1 | F | F | 3 | 3-CONHCH$_3$ | 2,6-dichlorophenyl | mp. 101.5° C. |
| 17 | 1 | F | F | 4 | 2-CONH$_2$ | 2,4,6-trimethylphenyl | mp. 127.2° C. |
| 18 | 4 | F | F | 3 | 3-CONHCH$_3$ | 2-acetyl-6-chlorophenyl | .2(ethanedioate); mp. 140° C. |

B. Pharmacological Example

Example B.1

The pain-relieving potential of the compounds of formula (I) was assesed using the "formalin test" on guinea pigs. Female guinea pigs (280–320 g) were starved overnight, weighed and placed in an observation cage. One hour after intraperitoneal injection of a compound of formula (I),, a 5% formalin solution (0.05 ml) was injected in the right hindpaw of the guinea pig. During 5 minutes the flinching and licking responses were counted. Over the next 25% minutes, the eyereflex and effect on muscle tone was recorded. The left hindpaw of the guinea pig was also injected with 0.05 ml of a 5% solution of formalin and the same observations were recorded. Afterwards, the animals were sacrificed. The estimated effective lowest dose of the compounds 1 to 18, whereby the number of pain-induced responses was reduced by more than 50%, ranged between 0.63 and 40 mg/kg body weight.

What is claimed is:

1. A method of treating warm-blooded animals suffering from chronic pain conditions comprising administering to said animals an effective amount of a nucleoside transport inhibitor.

2. The method according to claim 1 wherein the nucleoside transport inhibitor is a compound of formula (I)

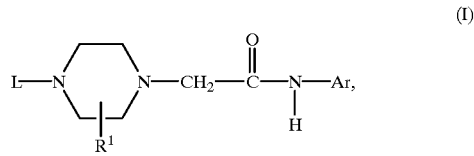

an N-oxide form, a pharmaceutically acceptable acid addition salt or a stereochemically isomeric form thereof, wherein R$^1$ is C$_{1-4}$alkyl, aminocarbonyl or mono- or di(C$_{1-4}$alkyl) aminocarbonyl;

L is a radical of formula

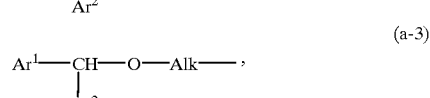

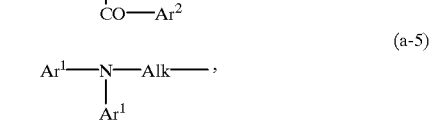

-continued

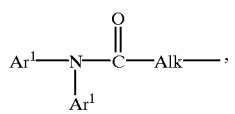
(a-6)

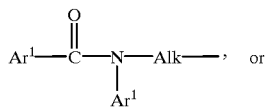
(a-7)

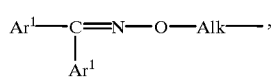
(a-8)

wherein
Ar$^1$ is phenyl, phenyl substituted with halo or C$_{1-4}$alkyloxy;
Ar$^2$ is phenyl; phenyl substituted with halo, C$_{1-4}$alkyloxy; or pyridinyl;
Alk is C$_{1-4}$alkanediyl;
Ar is a radical of formula

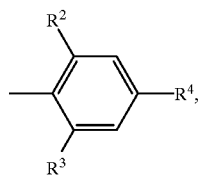
(b-1)

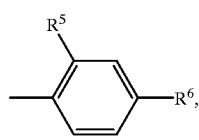
(b-2)

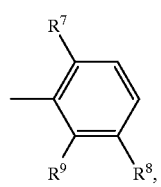
(b-3)

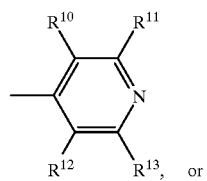
(b-4)

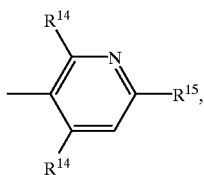
(b-5)

wherein
R$^2$ and R$^3$ each independently are halo or C$_{1-4}$alkyl;
R$^4$ is hydrogen, halo, nitro, amino, mono- or di(C$_{1-4}$alkyl)amino, C$_{1-4}$alkylcarbonylamino, aminocarbonylamino, C$_{1-4}$alkyl, C$_{1-4}$alkyloxy, C$_{1-4}$alkyloxycarbonyl, C$_{1-4}$alkylcarbonyl, aminocarbonyl, mono- or di(C$_{1-4}$alkyl)aminocarbonyl, cyano or aminomethyl;

R$^5$ is C$_{1-4}$alkylcarbonyl;

R$^6$ is hydrogen, amino, mono- or di(C$_{1-4}$alkyl)amino, C$_{1-4}$alkylcarbonylamino, aminocarbonylamino, aminocarbonyl or cyano;

R$^7$ is C$_{1-4}$alkyl;

R$^8$ is halo or C$_{1-4}$alkylcarbonyl;

R$^9$ is hydrogen or C$_{1-4}$alkyl;

R$^{10}$ is halo or C$_{1-4}$alkyl;

R$^{11}$ is hydrogen, hydroxy or C$_{1-4}$alkyl;

R$^{12}$ is halo or C$_{1-4}$alkyl;

R$^{13}$ is hydrogen or;

R$^{12}$ and R$^{13}$ taken together may also form a C$_{3-5}$alkanediyl radical;

each R$^{14}$ is C$_{1-4}$alkyl; and

R$^{15}$ is C$_{1-4}$alkyl or amino.

3. The method according to claim 2 wherein R$^1$ is aminocarbonyl or (C$_{1-4}$alkyl)aminocarbonyl; L is a radical of formula (a-1) or (a-2) wherein Ar$^1$ is phenyl or phenyl substituted with halo; Ar$^2$ is phenyl, phenyl substituted with halo, or pyridinyl; Alk is C$_{1-4}$alkanediyl; Ar is a radical of formula (b-1) or (b-3) wherein R$^2$ and R$^3$ each independently are halo or C$_{1-4}$alkyl; R$^4$ is hydrogen, C$_{1-4}$alkyl, halo, nitro, amino, cyano or aminocarbonyl; R$^7$ is C$_{1-4}$alkyl; R$^8$ is halo or C$_{1-4}$alkyl-carbonyl; and R$^9$ is hydrogen or C$_{1-4}$alkyl.

4. The method according to claim 2 wherein R$^1$ is aminocarbonyl or methylaminocarbonyl; L is a radical of formula (a-1) or (a-2) wherein Ar$^1$ is phenyl or phenyl substituted with fluoro; Ar$^2$ is phenyl, phenyl substituted with fluoro, or pyridinyl; Alk is C$_{3-4}$alkanediyl; Ar is a radical of formula (b-1) or (b-3) wherein R$^2$ and R$^3$ each independently are chloro or methyl; R$^4$ is hydrogen, methyl, chloro, amino, cyano or aminocarbonyl; R$^7$ is methyl; R$^8$ is chloro or methylcarbonyl; and R$^9$ is hydrogen.

5. The method according to claim 2 wherein the compound is 2-(aminocarbonyl)-N-(4-amino-2,6-dichlorophenyl)-4-[5,5-bis(4-fluorophenyl)-pentyl]-1-piperazineacetamide; or S-(−)-2-(aminocarbonyl)-N-(4-amino-2,6-dichlorophenyl)-4-[5,5-bis(4-fluorophenyl)-pentyl]-1-piperazineacetamide; the stereochemically isomeric forms, pharmaceutically acceptable acid addition salts and the N-oxide forms thereof.

6. The method according to claim 1 wherein the chronic pain condition is neuropathic pain.

7. A product containing
a) a composition comprising a therapeutically effective amount of a compound according to claim 2 and a pharmaceutically acceptable carrier; and
b) a composition comprising a therapeutically effective amount of an analgesic and a pharmaceutically acceptable carrier, as a combined preparation for simultaneous, separate or sequential use in the treatment of pain.

8. A compound of formula (I),

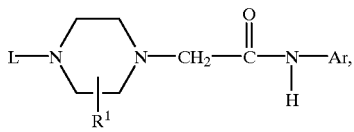

wherein the compound is
N-(2-acetyl-6-chlorophenyl)-4-[5,5-bis(4-fluorophenyl)-4-pentenyl]-3-[(methyl-amino)carbonyl]-1-piperazineacetamide; the stereochemically isomeric forms, pharmaceutically acceptable acid addition salts and the N-oxide forms thereof.

9. A pharmaceutical composition comprising a therapeutically effective amount of a compound as claimed in claim 8 and a pharmaceutically acceptable carrier.

10. The method according to claim 3 wherein $R^1$ is aminocarbonyl or methylaminocarbonyl; L is a radical of formula (a-1) or (a-2) wherein $Ar^1$ is phenyl or phenyl substituted with fluoro; $Ar^2$ is phenyl, phenyl substituted with fluoro, or pyridinyl; Alk is $C_{3-4}$alkanediyl; Ar is a radical of formula (b-1) or (b-3) wherein $R^2$ and $R^3$ each independently are chloro or methyl; $R^4$ is hydrogen, methyl, chloro, amino, cyano or aminocarbonyl; $R^7$ is methyl; $R^8$ is chloro or methylcarbonyl; and $R^9$ is hydrogen.

* * * * *